United States Patent
Ekström

(10) Patent No.: US 9,295,644 B2
(45) Date of Patent: Mar. 29, 2016

(54) METHODS AND COMPOSITIONS FOR TREATING ASTHMA

(75) Inventor: Tommy Ekström, Linköping (SE)

(73) Assignee: AstraZeneca AB, Södertälje (SE)

( * ) Notice: Subject to any disclaimer, the term of this patent is extended or adjusted under 35 U.S.C. 154(b) by 1806 days.

(21) Appl. No.: 10/665,240

(22) Filed: Sep. 19, 2003

(65) Prior Publication Data

US 2004/0063676 A1    Apr. 1, 2004

Related U.S. Application Data

(63) Continuation of application No. 09/367,950, filed as application No. PCT/SE99/01031 on Jun. 10, 1999, now abandoned.

(30) Foreign Application Priority Data

Jun. 11, 1998 (SE) ...................................... 9802073

(51) Int. Cl.

| | |
|---|---|
| *A01N 45/00* | (2006.01) |
| *A61K 31/56* | (2006.01) |
| *A61K 31/585* | (2006.01) |
| *A01N 33/18* | (2006.01) |
| *A01N 33/24* | (2006.01) |
| *A61K 31/045* | (2006.01) |
| *A01N 31/00* | (2006.01) |
| *A61K 9/00* | (2006.01) |
| *A61K 31/58* | (2006.01) |
| *A61K 45/06* | (2006.01) |
| *A61K 9/14* | (2006.01) |

(52) U.S. Cl.
CPC ............... *A61K 9/0075* (2013.01); *A61K 31/58* (2013.01); *A61K 45/06* (2013.01); *A61K 9/145* (2013.01)

(58) Field of Classification Search
CPC . A61K 31/38; A61K 2300/00; A61K 31/165; A61K 45/06; A61K 9/75; A61K 9/145
USPC ........................... 514/727, 730, 169, 171, 174
See application file for complete search history.

(56) References Cited

U.S. PATENT DOCUMENTS

| | | | |
|---|---|---|---|
| 4,203,401 A | 5/1980 | Kingsley et al. | |
| 5,119,791 A | 6/1992 | Gifford et al. | |
| 5,250,286 A | 10/1993 | Skupin | |
| 5,408,977 A | 4/1995 | Cotton | |
| 5,511,957 A | 4/1996 | Tuckey et al. | |
| 5,651,349 A | 7/1997 | Dykstra et al. | |
| 5,674,860 A | 10/1997 | Carling et al. | |
| 5,684,199 A | 11/1997 | Francotte | |
| 5,795,564 A * | 8/1998 | Aberg et al. ..................... 424/45 |
| 5,924,410 A | 7/1999 | Dumas et al. | |
| 5,957,114 A | 9/1999 | Johnson et al. | |
| 5,972,919 A | 10/1999 | Carling et al. | |
| 5,983,956 A * | 11/1999 | Trofast .............................. 141/1 |
| 5,996,576 A | 12/1999 | Yule | |
| 6,030,604 A | 2/2000 | Trofast | |
| 6,136,075 A | 10/2000 | Bragg et al. | |
| 6,237,574 B1 | 5/2001 | Jamrog et al. | |
| 6,277,862 B1 | 8/2001 | Giardina et al. | |
| 6,302,144 B1 | 10/2001 | Graham et al. | |
| 6,343,590 B1 | 2/2002 | Nagai et al. | |
| 6,374,811 B1 | 4/2002 | Mancini | |
| 6,598,603 B1 | 7/2003 | Andersson et al. | |

FOREIGN PATENT DOCUMENTS

| | | |
|---|---|---|
| CA | 2123909 | 6/1993 |
| CA | 2356145 | 6/1993 |
| EP | 0 416 950 A1 | 3/1991 |
| EP | 0 416 951 A1 | 3/1991 |
| EP | 0 523 638 | 1/1993 |
| EP | 1085877 | 12/1999 |
| EP | 1 014 993 | 7/2000 |
| EP | 0613371 | 3/2002 |
| SE | 9703407-8 | 9/1997 |
| WO | WO 92/11280 | 7/1992 |

(Continued)

OTHER PUBLICATIONS

Ryrfeldt et al. "Pulmonary disposition of the potent glucocorticoid developed for the local treatment of☐☐respiratory disorders such as bronchial asthma and allergic rhinitis" Biochem. Pharmacol., 1989, 38(1), 17-☐☐22.*

(Continued)

*Primary Examiner* — Kendra D Carter
(74) *Attorney, Agent, or Firm* — Morgan, Lewis & Bockius LLP

(57) ABSTRACT

The present invention relates to use of a composition for symptomatic relief, when needed, comprising, in admixture
(a) a first active ingredient which is formoterol, a pharmaceutically acceptable salt or solvate thereof or a solvate of such a salt; and
(b) a second active ingredient which is budesonide;
for the manufacture of a medicament for use in the prevention or treatment of an acute condition of asthma and/or intermittent asthma and/or episodes in chronic asthma. The invention further relates to a method for prevention or treatment of an acute condition of asthma and/or intermittent asthma and/or episodes in chronic asthma by administering, by inhalation, a composition comprising the first and second active ingredients as defined previously.

42 Claims, No Drawings

(56) References Cited

FOREIGN PATENT DOCUMENTS

| WO | WO 9311773 A1 * | 6/1993 |
|----|----|----|
| WO | WO 98/15280 | 4/1998 |
| WO | WO 98/31351 | 7/1998 |
| WO | WO 99/00134 | 1/1999 |
| WO | WO99/64014 | 12/1999 |
| WO | WO 00/30608 | 6/2000 |
| WO | WO 00/35441 | 6/2000 |
| WO | WO 00/53188 | 9/2000 |

OTHER PUBLICATIONS

Arvidsson et al., "Inhaled formoterol during one year in asthma: a comparison with salbutamol," Eur Respir J, 4:1168-1173, 1991.

Aubier et al., "Salmeterol/Fluticasone propionate (50/500 μg) in combination in a Diskus inhaler (Seretide) is effective and safe in the treatment of steroid-dependent asthma," Respir. Med. 93:876-884, 1999.

Bartow et al., "Formoterol: An Update of its Pharmacological Properties and Therapeutic Efficacy in the Management of Asthma," Drugs, 55(2):303-322, 1998.

Bond, "A strategy that works," New Zealand Medical Journal, p. 369, Aug. 28, 1991.

Corren et al., "Twelve-Week, Randomized, Placebo-Controlled, Multicenter Study of the Efficacy and Tolerability of Budesonide and Formoterol in One Metered-Dose Inhaler Compared with Budesonide Alone and Formoterol Alone in Adolescents and Adults with Asthma," Clinical Therapeutics, 29(5):823-843, 2007.

Costain et al., "Guidelines for management of asthma in adults: I—chronic persistent asthma," BMJ, 301:651-653, 1990.

Ebden et al., "Comparison of two high dose corticosteroid aerosol treatments, beclomethasone dipropionate (500 μg/day) and budesonide (1600 μg/day), for chronic asthma," Thorax, 41:869-874, 1986.

"FDA recommends easier-to-take asthma drug" Florida Today, Associate Press, Nov. 24, 1999.

"Foradil: Fast relief that lasts," Ciba-Geigy Limited, Switzerland, Medical and Pharmaceutical Information, 1993.

Hekking et al. presentation, "Efficacy and tolerability of inhaled formoterol compared with inhaled salbutamol over three months", Symposium held during the 8$^{th}$ congress of the European Society of Pneumology, Freiberg, Germany, Sep. 1989.

Jackson et al., "Benefit-Risk Assessment of Long-Acting $\beta_2$-Agonists in Asthma," Drug Safety, 27(4):243-270, 2004.

Kesten et al., "A Three-Month Comparison of Twice Daily Inhaled Formoterol Versus Four Times Daily Inhaled Albuterol in the Management of Stable Asthma," Am Rev Respir Dis, 144:622-625, 1991.

Kumar et al., "Transient Effect of Inhaled Fluticasone on Airway Mucosal Blood Flow in Subjects with and without Asthma," Am J Respir Crit Care Med, 161:918-921, 2000.

Lampa et al., "Antitracheobronchospastic Interaction In Vitro and In Vivo between Salbutamol and Flunisolide," Drugs Exptl. Clin. Res., XI(9):653-658, 1985.

McDonald et al., "Evaluation of the combination inhaler of salbutamol and beclomethasone dipropionate in the management of asthma," Curr. Med. Res. Opin., 11(2):116-122, 1988.

McFadden, "Inhaled Glucocorticoids and Acute Asthma: Therapeutic Breakthrough or Nonspecific Effect?," Am J Respir Crit Care Med, 157:677-678, 1998.

Monthly Index of Medical Specialties (MIMS), Asthma, COPD, Sep. 2007.

Monthly Index of Medical Specialties (MIMS), Bronchodilators and anti-inflammatories, Dec. 1991.

Monthly Index of Medical Specialties (MIMS), Respiratory System, Dec., 1991.

Moore et al., "Long-acting Inhaled $\beta_2$-Agonists in Asthma Therapy," Chest, 113:1095-1108, 1998.

Nyholm et al., "Therapeutic advantages of twice-daily over four-times daily inhalation budesonide in the treatment of chronic asthma," Eur J Respir Dis, 65:339-345, 1984.

Rabe et al., "The challenge of long-acting β-adrenoceptor agonists," Respiratory Medicine, 85:5-9, 1991.

Rabe et al., "Effect of budesonide in combination with formoterol for reliever therapy in asthma exacerbations: a randomized controlled, double-blind study," Lancet, 368:744-753, 2006.

Rabe et al., "Budesonide/Formoterol in a Single Inhaler for Maintenance and Relief in Mild-to-Moderate Asthma," Chest, 129:246-256, 2006.

Rees, "$\beta_2$ Agonists and asthma," BMJ, 302:1166-1167, 1991.

Rodrigo et al., "Inhaled Flunisolide for Acute Severe Asthma," Am J Respir Crit Care Med, 157:698-703, 1998.

Rodrigo et al., "Acute Asthma in Adults: A Review," Chest, 125:1081-1102, 2004.

Sears et al., "Regular inhaled beta-agonist treatment in bronchial asthma," Lancet, 336:1391-1396, 1990.

Shepherd et al., "Regular Versus Symptomatic Aerosol Bronchodilator Treatment of Asthma", Br. J. Dis. Chest, vol. 75, pp. 215-217 (1981).

Tan et al., "Systemic Corticosteroid Rapidly Reverses Bronchodilator Subsensitivity induced by Formoterol in Asthmatic Patients", Am. J. Respiratory and Critical Care Medicine, 156:28-35, 1997.

The Dialog Corporation, "Formoterol launched in Switzerland", Accession No: S002557609000, Oct. 31, 1990.

The Merck Manual of Diagnosis and Therapy, 16$^{th}$ edition, 1992, p. 653.

Trechsel, "Foradil in medical practice: 7 case studies," British J. Pharmacol., vol. 83 (1984).

Waalkens et al., "Budesonide and terbutaline or terbutaline alone in children with mild asthma: effects on bronchial hyperresponsiveness and diurnal variation in peak flow," Thorax, 46:499-503, 1991.

Wallin et al., "Formoterol, a new long acting beta2 agonist for inhalation twice daily, compared with salbutamol in the treatment of asthma," Thorax, 45:259-261, 1990.

Morice et al., "A comparison of nebulized budesonide with oral prednisolone in the treatment of exacerbations of obstructive pulmonary disease", Clinical Pharmacology & Therapeutics vol. 60, pp. 675-678 (1996).

Ankerst et al., "Tolerability of a High Dose of Budesonide/Formoterol in a Single Inhaler in Patients with Asthma," manuscript (24 pages), as submitted for publication to Pulm. Pharm. Ther. with letter dated Feb. 6, 2003 to the EPO, later published as vol. 16(3), pp. 147-151 (2003).

Ankerst et al., "Tolerability of a High Dose of Budesonide/Formoterol in a Single Inhaler in Patients with Asthma," Pulm. Pharm. Ther. vol. 16(3):147-151 (2003) (abstract only).

Bjermer et al., "Long-acting $\beta_2$-agonists: how they are used in an optimal way?," Respiratory Medicine, vol. 91, pp. 587-591 (1997).

Bourbeau et al., "Randomised controlled trial of inhaled corticosteroids in patients with chronic obstructive pulmonary disease", Thorax, vol. 53, pp. 477-482 (1998).

Clinical Practice Guidelines, Expert Panel Report 2, Guidelines for the Diagnosis and Management of Asthma, NIH Publication No. 97-4051, Jul. 1997.

Corden and Rees, "The effect of oral corticosteroids on bronchodilator responses in COPD," Respiratory Medicine, vol. 92, pp. 279-282 (1998).

Haughney et al., "Adjustable maintenance treatment with budesonide/formoterol combination rapidly improves and maintains quality of life in asthma patients," European Respiratory Society Annual Congress (ERS) Stockholm, Sep. 14-18, 2002, Poster Presentation, P379, submitted to EPO with letter dated Feb. 6, 2003.

Ind et al., "Managed Adjustable closing of budesonide/formoterol combination provides equivalent asthma control to fixed dosing at a lower overall dose," European Respiratory Society Annual Congress (ERS) Stockholm, Sep. 14-18, 2002, Poster Presentation, P2450, submitted to EPO with letter dated Feb. 6, 2003.

Letter from AstraZeneca to EPO dated Feb. 6, 2003 in EP Application 99930103.9.

Lipworth, "A Single High Dose of Budesonide Rapidly Reverses Bronchoprotective Subsensitivity and B2-Adrenocepter Down-Regulation in Patients Receiving Regular Formoterol," J. Allergy Clin. Immunol., p. S152, Section 629, Jan. 1998.

(56) References Cited

OTHER PUBLICATIONS

Lipworth, "Airway Subsensitivity with Long-Acting β2-Agonists," Drug Safety, vol. 16(5), pp. 295-308 (1997).
Lipworth et al., "Effects of Treatment with Formoterol on Bronchoprotection against Methacholine," Amer. J. Med., vol. 104, pp. 431-438 (1998).
Löfdahl et al., "Long-acting $\beta_2$-adrenoceptor agonists: a new perspective in the treatment of asthma," The European Respiratory Journal, vol. 4, pp. 218-226 (1991).
O'Byrne et al., "Additive Effects of Budesonide and Formoterol in Reducing Severe Asthma Exacerbations over 12 Months," abstract of presentation given at the Jun. 1-5, 1997, Annual Meeting of Allergology and Clinical Immunology, published as abstract 266 in Allergy 52, Supp. 37-89 (1997).
Olsson et al., "Adjustable maintenance treatment of asthma with budesonide and formoterol in a single inhaler," European Respiratory Society Annual Congress (ERS) Stockholm, Sep. 14-18, 2002, Poster Presentation, P2451, submitted to EPO with letter dated Feb. 6, 2003.
Paggiaro et al., "Multicentre randomised placebo-controlled trial of inhaled fluticasone propionate in patients with chronic obstructive pulmonary disease," The Lancet, vol. 351, pp. 773-780 (1998).
Price et al., "Budesonide/formoterol with an adjustable maintenance plan costs less and is as effective as fixed dosing," European Respiratory Society Annual Congress (ERS) Stockholm, Sep. 14-18, 2002, Poster Presentation, P2452, submitted to EPO with letter dated Feb. 6, 2003.
Rosenhall et al., "Efficacy, safety and cost of budesonide/formoterol in a single inhaler compared with budeonside plus formoterol as separate inhalers", European Respiratory Society Annual Congress (ERS) Stockholm, Sep. 14-18, 2002, Poster Presentation, P388, submitted to EPO with letter dated Feb. 6, 2003.
Scrip, The Dialog Corporation, 1562, p. 21 (Oct. 31, 1990).
Sung et al., "Randomized, Controlled Trial of Inhaled Budesonide as an Adjunct to Oral Prednisone in Acute Asthma", Academic Emergency Medicine, vol. 5(3), pp. 209-212 (1998).
Wempe et al., "Effects of corticosteroids on bronchodilator action in chronic obstructive lung disease," Thorax, vol. 47, pp. 616-621 (1992).
Decision of the EPO Opposition Division regarding patent EP-B-1210943, dated Dec. 5, 2008.
Statement of Grounds of Opposition to patent EP1085877 by Vectura Limited, received at the EPO on Dec. 17, 2008.
Statement of Grounds of Opposition to patent EP1085877by Generics Limited, received at the EPO on Dec. 19, 2008.
Statement of Grounds of Opposition to patent EP1085877 by Norton Health Care Limited, received at the EPO on Dec. 19, 2008.
Statement of Grounds of Opposition to patent EP1085877 by Ratiopharm GmbH, received at the EPO on Dec. 17, 2008, translation attached.
Response by Astra to EPO, dated Nov. 22, 1995.
"What You Should Know About Symbicort Turbohaler?," AstraZeneca, May 2001, 4 pages.
U.S. Examiner Rebecca Cook, Office Action in U.S. Appl. No. 09/194,290, mailed Aug. 16, 1999 (Rescinded) (5 pages).
U.S. Examiner Rebecca Cook, Office Action in U.S. Appl. No. 09/194,290, mailed Mar. 27, 2000 (case abandoned Oct. 2, 2000) (6 pages).
U.S. Examiner Rebecca Cook, Office Action in U.S. Appl. No. 09/670,457, mailed May 10, 2001 (case abandoned Nov. 30, 2001) (6 pages).
U.S. Examiner Jennifer M. Kim, Office Action in U.S. Appl. No. 09/367,950, mailed Dec. 18, 2000 (9 pages).
Fish & Richardson P.C., Amendment in Reply to Office Action dated Dec. 18, 2000, in U.S. Appl. No. 09/367,950, filed Apr. 18, 2001 (8 pages).
U.S. Examiner Jennifer M. Kim, Final Office Action in U.S. Appl. No. 09/367,950, mailed May 21, 2001 (8 pages).
Fish & Richardson P.C., Response to Final Office Action dated May 21, 2001, in U.S. Appl. No. 09/367,950, filed Aug. 21, 2001 (4 pages).
U.S. Examiner Jennifer M. Kim, Office Action in U.S. Appl. No. 09/367,950, mailed Sep. 25, 2001 (8 pages).
Fish & Richardson P.C., Response to Office Action dated May 21, 2001, in U.S. Appl. No. 09/367,950, filed Dec. 26, 2001 (3 pages).
U.S. Examiner Jennifer M. Kim, Final Office Action in U.S. Appl. No. 09/367,950, mailed Apr. 15, 2002 (6 pages).
U.S. Examiner Jennifer M. Kim, Interview Summary dated Sep. 17, 2002 in U.S. Appl. No. 09/367,950 (1 page).
Fish & Richardson P.C., Notice of Appeal in U.S. Appl. No. 09/367,950, filed Oct. 9, 2002 (1 page).
Fish & Richardson P.C., Request for Continued Examination and Amendment in Reply in U.S. Appl. No. 09/367,950, filed Dec. 10, 2002 (55 pages).
U.S. Examiner Jennifer M. Kim, Office Action in U.S. Appl. No. 09/367,950, mailed Mar. 21, 2003 (9 pages).
Fish & Richardson P.C., Response to Office Action dated Mar. 21, 2003, in U.S. Appl. No. 09/367,950, filed Jun. 19, 2003 (9 pages).
Fish & Richardson P.C., Supplemental Amendment filed Jul. 3, 2003, in U.S. Appl. No. 09/367,950 (8 pages).
U.S. Examiner Jennifer M. Kim, Notice of Allowance mailed Jul. 9, 2003, in U.S. Appl. No. 09/367,950 (9 pages).
U.S. Examiner Jennifer M. Kim, Office Action in U.S. Appl. No. 09/367,950, mailed May 4, 2004 (12 pages).
Fish & Richardson P.C., Reply to Office Action dated May 4, 2004, in U.S. Appl. No. 09/367,950, filed Nov. 1, 2004 (6 pages).
U.S. Examiner Jennifer M. Kim, Office Action in U.S. Appl. No. 09/367,950, mailed Mar. 30, 2005 (14 pages).
Fish & Richardson P.C., Amendment in Reply to Office Action dated Mar. 30, 2005, in U.S. Appl. No. 09/367,950, filed Jun. 29, 2005 (17 pages).
U.S. Examiner Jennifer M. Kim, Office Action in U.S. Appl. No. 09/367,950, mailed Sep. 21, 2005 (15 pages).
Fish & Richardson P.C., Amendment in Reply to Office Action dated Sep. 21, 2005, in U.S. Appl. No. 09/367,950, filed Nov. 15, 2005 (12 pages).
U.S. Examiner Jennifer M. Kim, Advisory Action in U.S. Appl. No. 09/367,950, mailed Dec. 14, 2005 (3 pages).
Fish & Richardson P.C., Brief on Appeal filed Mar. 3, 2006, in U.S. Appl. No. 09/367,950, filed Mar. 3, 2006 (61 pages).
U.S. Examiner Jennifer M. Kim, Examiner's Answer in U.S. Appl. No. 09/367,950, mailed Jun. 16, 2006 (15 pages).
Fish & Richardson P.C., Reply Brief on Appeal filed Aug. 14, 2006, in U.S. Appl. No. 09/367,950 (15 pages).
U.S. Examiner Jennifer M. Kim, Communication regarding Appeal Brief in U.S. Appl. No. 09/367,950, mailed Sep. 12, 2006 (2 pages).
U.S. Examiner Jennifer M. Kim, Notice of Non-Compliant Appeal Brief in U.S. Appl. No. 09/367,950, mailed Oct. 30, 2006 (4 pages).
Fish & Richardson P.C., Amendment in Reply to Non-Compliant Appeal Brief dated Oct. 30, 2006, in U.S. Appl. No. 09/367,950, filed Nov. 28, 2006 (8 pages).
U.S. Examiner Jennifer M. Kim, Office Communication dated Jan. 24, 2007, in U.S. Appl. No. 09/367,950 (2 pages).
Board of Patent Appeals and Interferences, Order remanding to the Examiner, in U.S. Appl. No. 09/367,950, dated Aug. 28, 2007 (11 pages).
U.S. Examiner Jennifer M. Kim, Interview Summary mailed Oct. 22, 2007, in U.S. Appl. No. 09/367,950 (4 pages).
Fish & Richardson P.C., Interview Summary Following Board Decision of Aug. 28, 2007, dated Nov. 9, 2007 and re-filed Nov. 21, 2007 in U.S. Appl. No. 09/367,950 (13 pages).
U.S. Examiner Jennifer M. Kim, Office Action in U.S. Appl. No. 09/367,950, mailed Dec. 4, 2007 (16 pages).
Fish & Richardson P.C., Amendment in Reply to Office Action dated Dec. 4, 2007, in U.S. Appl. No. 09/367,950, filed Jun. 3, 2008 (37 pages).
U.S. Examiner Jennifer M. Kim, Final Office Action in U.S. Appl. No. 09/367,950, mailed Oct. 6, 2008 (21 pages).
Fish & Richardson P.C., Amendment in Reply to Final Office Action dated Oct. 6, 2008, in U.S. Appl. No. 09/367,950, filed Apr. 3, 2009 (20 pages).
Fish & Richardson P.C., Preliminary Amendment, in U.S. Appl. No. 10/010,283, filed Nov. 13, 2001 (4 pages).

(56) References Cited

OTHER PUBLICATIONS

U.S. Examiner Jennifer M. Kim, Office Action in U.S. Appl. No. 10/010,283, mailed Jan. 29, 2002 (10 pages).
Fish & Richardson P.C., Amendment in Reply to Office Action dated Jan. 29, 2002 together with Second Preliminary Amendment and Declarations of Jan Trofast, Lisa Woodson and Celia Leber in U.S. Appl. No. 10/010,283, filed Apr. 25, 2002 (56 pages).
U.S. Examiner Jennifer M. Kim, Office Action in U.S. Appl. No. 10/010,283, mailed Jul. 30, 2002 (8 pages).
Fish & Richardson P.C., Amendment in Reply to Office Action dated Jul. 30, 2002, in U.S. Appl. No. 10/010,283, filed Dec. 2, 2002 (8 pages).
Fish & Richardson P.C., Supplemental Remarks in Reply to Office Action dated Jul. 30, 2002, in U.S. Appl. No. 10/010,283, filed Dec. 13, 2002 (13 pages).
U.S. Examiner Jennifer M. Kim, Final Office Action in U.S. Appl. No. 10/010,283, mailed Jan. 29, 2003 (6 pages).
U.S. Examiner Jennifer M. Kim, Interview Summary in U.S. Appl. No. 10/010,283, mailed Jun. 3, 2003 (1 page).
Fish & Richardson P.C., Notice of Appeal, in U.S. Appl. No. 10/010,283, filed Jun. 27, 2003 (1 page).
Fish & Richardson P.C., Brief on Appeal, in U.S. Appl. No. 10/010,283, filed Sep. 26, 2003 (10 pages).
U.S. Examiner Jennifer M. Kim, Examiner's Answer Before the Board Patent Appeals and Interferences, in U.S. Appl. No. 10/010,283, mailed Dec. 29, 2003 (13 pages).
Fish & Richardson P.C., Submission Under 37 CFR 1.114(c) together with Declaration of Jan Trofast, in U.S. Appl. No. 10/010,283, filed Mar. 1, 2004 (13 pages).
U.S. Examiner Jennifer M. Kim, Office Action in U.S. Appl. No. 10/010,283, mailed Jun. 18, 2004 (11 pages).
Fish & Richardson P.C., Reply to Office Action dated Jun. 18, 2004, in U.S. Appl. No. 10/010,283, filed Dec. 20, 2004 (42 pages).
Fish & Richardson P.C., Supplemental Reply to Office Action dated Jun. 18, 2004, in U.S. Appl. No. 10/010,283, filed Jan. 14, 2005 (2 pages).
U.S. Examiner Jennifer M. Kim, Office Action in U.S. Appl. No. 10/010,283, mailed May 4, 2005 (12 pages).
Fish & Richardson P.C., Proposed Claim Amendments for Interview in U.S. Appl. No. 10/010,283, filed Aug. 22, 2005 (9 pages).
U.S. Examiner Jennifer M. Kim, Interview Summary in U.S. Appl. No. 10/010,283, mailed Aug. 23, 2005 (1 page).
Fish & Richardson P.C., Amendment in Reply to Office Action dated May 4, 2005, in U.S. Appl. No. 10/010,283, filed Nov. 4, 2005 (36 pages).
Fish & Richardson P.C., Supplemental Petition to Accept Unintentionally Delayed Benefit Claim and Supplemental Amendment in Reply to Office Action, in U.S. Appl. No. 10/010,283, filed Mar. 15, 2006 (5 pages).
U.S. Examiner Jennifer M. Kim, Final Office Action in U.S. Appl. No. 10/010,283, mailed Jun. 15, 2006 (16 pages).
U.S. Examiner Jennifer M. Kim, Interview Summary in U.S. Appl. No. 10/010,283, mailed Oct. 26, 2006 (3 pages).
Fish & Richardson P.C., Amendment in Reply to Final Office Action dated Jun. 15, 2006 and Notice of Appeal, in U.S. Appl. No. 10/010,283, filed Nov. 15, 2006 (19 pages).
U.S. Examiner Jennifer M. Kim, Advisory Action, in U.S. Appl. No. 10/010,283, mailed Dec. 4, 2006 (9 pages).
Fish & Richardson P.C., Brief on Appeal and Request for Oral Hearing, in U.S. Appl. No. 10/010,283, filed Mar. 7, 2007 (118 pages).
U.S. Examiner Jennifer M. Kim, Ex Parte Quayle Action, in U.S. Appl. No. 10/010,283, mailed Jul. 12, 2007 (4 pages).
Fish & Richardson P.C., Amendment in Reply to Quayle Action dated Jul. 12, 2007, in U.S. Appl. No. 10/010,283, filed Jul. 27, 2007 (8 pages).
U.S. Examiner Jennifer M. Kim, Notice of Allowance, in U.S. Appl. No. 10/010,283, mailed Oct. 5, 2007 (7 pages).
U.S. Examiner Jennifer M. Kim, Notice of Allowance, in U.S. Appl. No. 10/010,283, mailed Feb. 26, 2008 (9 pages).
U.S. Examiner Jennifer M. Kim, Office Action, in U.S. Appl. No. 10/010,283, mailed Aug. 7, 2008 (15 pages).
Fish & Richardson P.C., Response to Office Action dated Aug. 7, 2008, in U.S. Appl. No. 10/010,283, filed Dec. 8, 2008 (18 pages).
U.S. Examiner Jennifer M. Kim, Notice of Allowance, in U.S. Appl. No. 10/010,283, mailed Mar. 13, 2009 (12 pages).
Fish & Richardson P.C., Reply to Office Action in U.S. Appl. No. 09/367,950, filed Dec. 21, 2009 (14 pages).
EPO Office Action from EP Serial No. 03 002 381.6-2123, dated Jun. 7, 2010 (5 pages).
Fish & Richardson P.C., Response to Final Office Action, in U.S. Appl. No. 09/367,950, filed Jun. 16, 2010 (22 pages).
U.S. Examiner Kendra D. Carter, Office Action in U.S. Appl. No. 10/010,283, mailed Mar. 5, 2010 (13 pages).
U.S. Examiner Jennifer M. Kim, Final Office Action in U.S. Appl. No. 09/367,950, mailed Mar. 17, 2010 (19 pages).
Barnes, "Chronic Obstructive Pulmonary Disease", Medical Progress, vol. 343(4), pp. 269-280 (2000).
Bateman et al, "Overall asthma control: The relationship between current control and future risk," J. Allergy Clin. Immunol., vol. 125(3), pp. 600-608e6 (2010).
Bousquet et al., "Budesonide/formoterol for maintenance and relief in uncontrolled asthma vs. high-dose salmeterol/fluticasone," Respiratory Medicine, vol. 101, pp. 2437-2446 (2007).
"BTS Guidelines for the Management of Chronic Obstructive Pulmonary Disease," Thorax, vol. 52(5), pp. S1-S28 (1997).
Calverley et al., "Preventing mortality in COPD: The value of inhaled budesonide added to bronchodilators." Presentation at COPD5, Birmingham, UK, Jun. 28, 2006, Abstract 35.
Cates et al. "Combination formoterol and budesonide as maintenance and reliever therapy versus inhaled steroid maintenance for chronic asthma in adults and children (Review)," Published by Wiley and Sons, Ltd., 64 pages (2010).
Chapman, "SMART isn't," J. Allergy Clin. Immunol.,vol. 125, pp. 609-610 (2010).
Dalby et al., "The bioavailability and airway clearance of the steroid component of budesonide/formoterol and salmeterol/fluticasone after inhaled administration in patients with COPD and healthy subjects: a randomized controlled trial," Respiratory Research, vol. 10(104), pp. 1-11 (2009).
"Definitions, Epidemiology, Pathophysiology, Diagnosis, and Staging," American Journal of Respiratory and Critical Care Medicine, vol. 152, pp. S78-S121 (1995).
D'Urzo, "Inhaled Glucocorticosteroid and Long-Acting β2-Adrenoceptor Agonist Single-Inhaler Combination for Both Maintenance and Rescue Therapy," Treat Respir Med, vol. 5, pp. 385-391 (2006).
Edwards et al., "Budesonide/formoterol for maintenance and reliever therapy of asthma: a meta analysis of randomised controlled trials," The International Journal of Clinical Practice, vol. 64(5), pp. 619-627 (2010).
Jones et al., "St George's respiratory questionnaire (SGRQ) scores may help identify COPD patients at increased risk of death over 1 year." Presentation at COPD5, Birmingham, UK, Jun. 28, 2006, Abstract 34.
Kuna et al., "Effect of budesonide/formoterol maintenance and reliever therapy on asthma exacerbations", Int. J. Clin. Pract., vol. 61(5), pp. 725-736 (2007).
Martin and Kraft, ed., Combination Therapy for Asthma and Chronic Obstructive Pulmonary Disease, Marcel Dekker, Inc., 2000, pp. 274-293.
Partridge et al., "Effect on lung function and morning activities of budesonide/formoterol versus salmeterol/fluticasone in patients with COPD," Therapeutic Advances in Respiratory Disease, vol. 3(4), pp. 147-157 (2009).
Pavord et al., "Airway inflammation in patients with asthma with high-fixed or low-fixed plus as-needed budesonide/formoterol," J. Allergy Clin. Immunol., vol. 123(5), pp. 1083-1089.e7 (2009).
Rabe et al., "Effect of budesonide in combination with formoterol for reliever therapy in asthma exacerbations: a randomised controlled, double-blind study," The Lancet, vol. 368, pp. 744-753 (2006).

(56) References Cited

OTHER PUBLICATIONS

Kennard et al., "Efficacy and Tolerability of Budesonide/Formoterol in One Hydrofluoroalkane Pressurized Metered-Dose Inhaler in Patients with Chronic Obstructive Pulmonary Disease," Drugs, vol. 69(5), pp. 549-565 (2009).
Scicchitano et al., "Efficacy and safety of budesonide/formoterol single inhaler therapy versus a higher dose of budesonide in moderate to severe asthma," Current Medical Research and Opinion, vol. 20(9), pp. 1403-1418 (2004).
Siafakas et al., "Optimal assessment and management of chronic obstructive pulmonary disease (COPD)," European Respiratory Journal, vol. 8, pp. 1398-1420 (1995).
Taylor et al., "A new perspective on concepts of asthma severity and control," Eur. Respir. J. vol. 32, pp. 545-554 (2008).
Tashkin et al., "Efficacy and Safety of Budesonide and Formoterol in One Pressurized Metered-Dose Inhaler in Patients with Moderate to Very Severe Chronic Obstructive Pulmonary Disease," Drugs, vol. 68(14); pp. 1975-2000 (2008).
Urbano, "Review of the NAEPP 2007 Expert Panel Report (EPR-3) on Asthma Diagnosis and Treatment Guidelines," Journal of Managed Care Pharmacy, vol. 14(1), pp. 41-49 (2008).
Venner Shipley LLP, Letter to the European Patent Office regarding opposition to EP Patent No. 1085877, filed by Generics (UK) Limited (Apr. 20, 2010).
Welte et al., "Efficacy and Tolerability of Budesonide/Formoterol Added to Tiotropium in Patients with Chronic Obstructive Pulmonary Disease," Am. J. Respir. Crit. Care Med., vol. 180, pp. 741-750 (2009).
Fish & Richardson, Response to Office Action mailed Mar. 5, 2010, in U.S. Appl. No. 10/010,283, filed Jun. 3, 2010 (23 pages).
Additive effects of Budesonide and Formoterol in Reducing Severe Asthma Exacerbations Over 12 Months, O'Byrne et al. on behalf of international study group and Astra Draco AB Lund Sweden, (Jun. 1997).
"American Thoracic Society: Standards for the Diagnosis and Care of Patients with Chronic Obstructive Pulmonary Disease," *Am. J Respir. Care Med*. 152:S77-S121 (1995).
"Analysis of DIN-LINK Co-prescription Records for Inhaled Steroids and Long-Acting Beta Agonists in the Period 1990-1998" pp. 1-2, appendices A and B.
"Atemstillstand" *Pschyrembel Klinisches Wörtebuch* (2002) (in German).
Auffarth et al., "Effects of inhaled budesonide on spirometric values, reversibility, airway responsiveness, and cough threshold in smokers with chronic obstructive lung disease" Thorax 46:372-377 (1991).
Barnes, "Inhaled steroids in COPD" The Lancet 351:766-767 (1998).
Barnes et al., "Chronic obstructive pulmonary disease: molecular and cellular mechanisms," Eur. Respir. J. 22:672-688 (2003).
Basic Reference Manual, vol. 1, revised ed. of 1988, issued by IMS International.
Boyd et al., "An Evaluation of Salmeterol in the Treatment of Chronic Obstructive Pulmonary Disease (COPD)," Eur. Resp. J. 10:815-821 (1997).
"Bronchodilators and anti-inflammatories," Monthly Index of Medical Specialities (MIMS) 242-256 (Sep. 1997).
Buist, "Definitions," in Asthma and Chronic Obstructive Pulmonary Disease, Barnes et al. eds., Acad. Press, pp. 3-6 (2002).
Burge et al. "Randomised, double blind, placebo controlled study of fluticasone propionate in patients with moderate to severe chronic obstructive pulmonary disease: the ISOLDE trial," British Med. J. 320:1297-1303 (2000).
Calverley et al., "Maintenance therapy with budesonide and formoterol in chronic obstructive pulmonary disease," Eur. Respir. J. 22:912-919 (2003).
Cazzola et al., "Effect of salmeterol and formoterol in patients with chronic obstructive pulmonary disease", Pulmonary Pharmacology, 1994, 7/2, pp. 103-107.
*Compendium Suisse des Medicaments*, 15$^{th}$ Ed. 1997/1998, Ed. Grand Public, compiled Jun. 1996, pp. 2-3, 419-429, 866 (in French).
*Compendium Suisse des Medicaments*, 18$^{th}$ Ed. 1997, Ed., compiled Jun. 1996, pp. 5, 849-851 and 1635-1636 (in French).
C. Wyser et al., "Neue Aspekte in der Behandlung des Asthma bronchiale and chronisch obstruktiver Lungenkrankheiten", 1997, Schweiz Med Wochenschr, vol. 127, pp. 885-890.
Davies et al., "Oral corticosteroid trials in the management of stable chronic obstructive pulmonary disease," Q. J. Med. 92:395-400 (1999).
Declaration of Professor N.B. Pride dated Aug. 4, 2004.
D.C. Flenley, "Today's Treatment of Airway Obstruction . . . and Tomorrow's?", Respiration, pp. 4-9 (1989).
"Disorders of the Airways," Current Medical Diagnosis and Treatment 1997 36th ed. pages 241-255, Stamford, CT: Appleton and Lange (1997).
Dompeling et al., "Slowing the deterioration of Asthma and Chronic Obstructive Pulmonary Disease Observed during Bronchodilator Therapy by Adding Inhaled Corticosteroids," Ann. Intern. Med. 118(10):770-778 (1993).
Engel et al., "A trial of inhaled budesonide on airway responsiveness in smokers with chronic bronchitis" Eur. Respir. J. 2:935-939 (1989).
Fabbri et al., "Global Strategy for the Diagnosis, Management and Prevention of COPD: 2003 update" Eur. Respir. J. 22:1-2 (2003).
Flenley, "Chronic Obstructive Pulmonary Disease," Disease-A-Month 34:549-599 (1988).
"Foradil" *Compendium Suisse des Medicaments*, Supplement 1 a pp. 7-8 (1991) (in French).
"Foradil," *Compendium Suisse des Medicaments*, 15th Ed. 1997/1998, Ed. Grand Public, compiled Jun. 1996, pp. 419-420, 866 (in French).
"Foradil," *Compendium Suisse des Medicaments*, 18th Ed. 1997, compiled Jun. 1996, pp. 849-850 and 1635 (in French).
"Foradil" Patient information leaflet, published by IKS, Switzerland (Dec. 1990) (in French).
"Foradil" MIMS—Monthly Index of Medical Specialties Jan. 10, (1996).
Gibson et al., Respiratory Medicine Table of contents (2002).
"GOLD: Global Initiative for Chronic Obstructive Lung Disease," Executive Summary; National Institutes of Health, National Heart Lung and Blood Institute, NIH Publication No. 2701A, pp. 1-30 (Mar. 2001).
"GOLD: Global Initiative for Chronic Obstructive Lung Disease; Global Strategy for the Diagnosis, Management, and Prevention of Chronic Obstructive Pulmonary Disease," based on Apr. 1998 NHLBI/WHO Workshop, pp. 1-100 (2004 Update).
Jackevicius et al., "Prehospitialization Inhaled Cortiscoteroid Use in Patients With COPD or Asthma" Chest 111:296-302 (1997).
Jeffery "Structural and inflammatory changes in COPD: a comparison with asthma" Thorax 53:129-136 (1998).
Keatings et al., "Effects of Inhaled and Oral Glucocorticoids on Inflammatory Indices in Asthma and COPD" Am. J. Respir. Crit. Care Med. 155:542-548 (1997).
Kerstjens et al., "A Comparison of Bronchodilator Therapy with or without Inhaled Corticosteroid Therapy for Obstructive Airways Disease," New Eng. J. Med. 327:1413-1419 (1992).
Leff et al., "Therapeutic Regimens in Chronic Obstructive Pulmonary Disease," Pulmon. Crit. Care Pharmacol. Therapeut. Ch. 86:837-844 (1996).
Minutes of the May 6, 2008 oral proceedings before the European Patent Office Technical Board of Appeal in the opposition against EP 1014993 (4 pages).
Nederlands Tijdschrift voor Geneeskunde "Opportunistic lung infection in patients with chronic obstructive pulmonary disease", 1996 140/2 pp. 94-98 ISSN: 0028-2162 CODEN: NET JAN.
New Ethicals Catalogue, Dec. 1990, No. 3, p. 50.
Niewoehner et al., "Effect of Systemic Glucocorticoids on Exacerbations of Chronic Obstructive Pulmonary Disease" New Eng. J. Med. 340(25):1941-1947 (1999).
Norman, "COPD: New Developments and Therapeutic Opportunities" *Drug News Perpect*. 11(7):431-437 (1998).
Pauwels et al., "Long-Term Treatment with Inhaled Budesonide in Persons with Mild Chronic Obstructive Pulmonary Disease Who Continue Smoking" N. Eng. J. Med. 340:1948-1953 (1999).

(56) References Cited

OTHER PUBLICATIONS

Pauwels, "COPD: The Scope of the Problem in Europe" Chest 117:332S-335S (2000).
Pearson et al., "British Thoracic Society Guidelines for Treatment of COPD" *Thorax* 52 (Suppl. 5):S1-S28 (1997).
Postma et al., "Rationale for the Dutch Hypothesis* Allergy and Airway Hyperresponsiveness as Genetic Factors and Their Interaction with Environment in the Development of Asthma and COPD", Chest, 126: 96S-104S (2004).
Postma, "Inhaled therapy in COPD: what are the benefits?" Respiratory Medicine 85:447-449 (1991).
"Pulmicort" ABPI Data Sheet Compendium, p. 146-147 (1995/1996).
Rabe, "Combination therapy for chronic obstructive pulmonary disease; one size fits all?" Eur. Respir. J. 22:874-875 (2003).
Renkema et al., "Effects of long-term treatment with corticosteroids in COPD", Chest, 1996, vol. 109, No. 5, abstract. AN 1996: 325104.
Renkema et al. "Key to the World's Chemical Literature", vol. 126, No. 20 (1997), CA (Chemical Abstracts) No. 259329.
Roberts et al., "Which patients are prescribed inhaled anti-asthma drugs?" *Thorax* 49(11):1090-1095 (1994).
Sauders Manual of Medical Practice. Rakel 1996.
Schultze-Werninghaus, "Multicenter 1-Year Trial on Formoterol, a New Long-Acting $\beta_2$-Agonist, in Chronic Obstructive Airway Disease," *Lung* Suppl:83-89 (1990).
Siafakas et al., "Optimal Assessment and Management of Chronic Obstructive Pulmonary Disease (COPD)," *Eur. Respir. J.* 8:1398-1420 (1995).
Soriano et al., "The Proportional Venn Diagram of Obstructive Lung Disease* Two Approximations From the United States and the United Kingdom", Chest 124: 474-481 (2003).
Soriano et al., "Inhaled Corticosteroids with/Without Long-Acting b-Agonists Reduce the Risk of Rehospitalization and Death in COPD Patients," *Am. J. Respir. Medic.* 2:67-74 (2003).
Stalenheim et al., "Efficacy and Tolerance of a 12-Week Treatment with Inhaled Formoterol in Patients with Reversible Obstructive Lung Disease," *Respiration* 61:305-309 (1994).
Statutory Declaration of Charles Richard William Beasley (1998).
Stedman's Medical Dictionary, 25th ed., Baltimore: Williams and Wilkins; p. 428 (1990).
Szafranski et al., "Efficacy and safety of budesonide/formoterol in the management of chronic obstructive pulmonary disease" *Eur. Respir. J.* 21:74-81 (2003).
The Merck Manual, sixteenth Edition, 1992, pp. 658-659.
Treschel, AM Conference Report, A new long-acting beta-stimulator (1991).
Van Schayck et al., "Do patients with COPD benefit from treatment with inhaled corticosteroids?" *Eur. Respir. J.* 9:1969-1972 (1996).
Van Andel et al., "Analysis of Inhaled Corticosteroid and Oral Theophylline Use Among Patients With Stable COPD from 1987 to 1995" *Chest* 115:703-707 (1999).
Vestbo et al., "Long-term effect of inhaled budesonide in mild and moderate chronic obstructive pulmonary disease: a randomised controlled trial," *Lancet* 353:1819-1823 (1999).
Vestbo et al., "Update on the "Dutch hypothesis", for chronic respiratory disease", *Thorax* 53(Suppl.2), S15-S19 (1998).
Watson et al. "Failure of Inhaled Corticosteroids to Modify Bronchoconstrictor or Bronchodilator Responsiveness in Middle-Aged Smokers with Mild Airflow Obstruction" *Chest* 101:350-355 (1992).
Weiner et al., "Inhaled Budesonide Therapy for Patients with Stable COPD," *Chest* 108:1568-1571 (1995).
Written decision of the European Patent Office Technical Board of Appeal in the opposition against EP 1014993, dated May 6, 2008 (17 pages).
Response to EPO Office Action in opposition against EP 108577, sent by AstraZeneca, dated Oct. 5, 2009 (17 pages).
Rabe et al., "Effect of budesonide in combination with formoterol for reliever therapy in asthma exacerbations: a randomized controlled, double-blind study," The Lancet, vol. 368, pp. 744-753 (2006) and slides based on Rabe et al.
Product insert for Advair Diskus®, Patient's Instructions for Use (3 pages), (2003).
Product insert for Symbicort® Turbuhaler® (2 pages), (1997).
Product insert for Pulmicort Turbuhaler® (4 pages), (1980).
Barnes, "A Single Inhaler for Asthma?," American Journal of Respiratory and Critical Care Medicine, vol. 171, pp. 95-96 (2005).
O'Bryne et al., "Budesonide/Formoterol Combination Therapy as Both Maintenance and Reliever Medication in Asthma," American Journal of Respiratory and Critical Care Medicine, vol. 171, pp. 129-136 (2005).
Chapter 2, Six-Part Asthma Management Program (International Consensus Report on Diagnosis and Management of Asthma), Allergy, vol. 47, suppl. 13, pp. 6-49 (1992).
Stephen Wasserman, M.D., "What Is A Rescue Medicine And When Is It Used To Treat Asthma?", ABC News, 2 pages, (Aug. 12, 2008).
Health Facts for You, Asthma Rescue Medicine, University of Wisconsin, Mar. 31, 2008 (2 pages).
Anthony D. D'Urzo, "Inhaled Glucocorticosteroid and Long-Acting $\beta_2$ Adrenoceptor Agonist Single-Inhaler Combination for Both Maintenance and Rescue Therapy", Treat. Respir. Med., vol. 5(6), pp. 385-391 (2006).
Kuna et al., "Effect of budesonide/formoterol maintenance and reliever therapy on asthma exacerbations", International Journal of Clinical Practice, vol. 61(5), pp. 725-736 (2007), and slides based on Kuna.
Tierney, et al., Disorders of the Airways, Current Medical Diagnosis and Treatment, Chapter 9, pp. 241-255, (1997).
Renkema et al., "Effects of Long-term Treatment With Corticosteroids in COPD," Chest, vol. 109, pp. 1156-1162 (1996).
Cochrane et al., "Bronchial asthma and the role of $\beta_2$-agonists", Respiratory Medicine, vol. 91(5), pp. 275-279 (1997).
Wilcke et al., "The effect of inhaled glucocorticosteroids in emphysema due to $\alpha_1$-antitrypsin deficiency", Respiratory Medicine, vol. 91, pp. 275-279 (1997).
Smeenk et al., Opportunistische longinfecties bij patiënten met chronishe obstructieve longziekte; een bijwerking van inhalatiecorticosteroïden?, *English translation included*, dated Mar. 11, 2003.
Wyser et al., Neu Aspekte in der Behandlung des Asthma bronchiale und chronisch obstruktiver Lungenkrankheiten, Schweiz-Med Wochenschr, vol. 127, pp. 885-890 (1997), *English Summary included*.
"Ventide Inhaler," ABPI Data Sheet Compendium, 1990-91 (3 pages).
Barnes, "A New Approach to the Treatment of Asthma," Drug Therapy, vol. 321(22), pp. 1515-1527 (2002).
"Foradil: Fast relief that lasts," Ciba-Geigy Limited, Switzerland, Medical and Pharmaceutical Information, Update 1994 (51 pages).
English Translation of Opposition filed against Chilean Patent Application No. 2744-2001 (3 pages).
Response to an Opposition in Chilean Application No. 2744/2001, dated Aug. 6, 2006, *English Translation included* (6 pages).
Request for Revocation of the Corresponding Patent in Turkey (TR 2000 00726), dated Jun. 6, 2009 (15 pages).
Notice of Opposition, filed by Ranbaxy Laboratories Limited, opposing the grant of Patent Application No. 190791 by Intellectual Property India (India Patent Office), dated Jun. 1, 2006 (21 pages).
Reply statement before the Opposition Board, Patent Office, Delhi; submitted on behalf of AstraZeneca, dated Jul. 27, 2006 (6 pages).
Affidavit of Jan William Trofast, before the Opposition Board, Patent Office, Delhi; submitted on behalf of AstraZeneca, dated Sep. 13, 2006 (7 pages).
Opponent Response in Opposition to Patent No. 19071, submitted by Lakshmi Kumaran & Sridharan, dated Nov. 3, 2006 (6 pages).
U.S. Examiner Jennifer M. Kim, Office Action in U.S. Appl. No. 09/367,950, mailed Jun. 25, 2009 (21 pages).
U.S. Examiner Jennifer M. Kim, Notice of Allowance in U.S. Appl. No. 10/010,283, mailed Aug. 28, 2009 (14 pages).

(56) References Cited

OTHER PUBLICATIONS

Fish & Richardson P.C., Request for Continued Examination from U.S. Appl. No. 10/010,283, filed Nov. 12, 2009 (1 page).
Ankerst et al., "Tolerability of a high dose of budesonide/formoterol in a single inhaler in patients with asthma," Pulm Phannacol Ther., 16:147-151, 2003.
"The British Guidelines on Asthma Management 1995 Review and Position Statement," Thorax, 52(Suppl 1):S1-21, 1997.
Collins et al., "The Use of Corticosteroids in the Treatment of Acute Asthma," Quarterly Journal of Medicine, New Series, XLIV:259-273, 1975.
Devidayal et al., "Efficacy of nebulized budesonide compared to oral prednisolone in acute bronchial asthma," Acta Paediatr, 88:835-840, 1999.
Ellul-Micallef and Johansson, "Acute Dose-Response Studies in Bronchial Asthma with a New Corticosteroid, Budesonide," Br. J. Clin. Phamtac., 15:419-422, 1983.
Ellul-Micallef et al., "Budesonide: A New Corticosteroid in Bronchial Asthma," Eur J Respir Dis., 61:167-173, 1980.
Engel et al., "Single-dose inhaled budesonide in subjects with chronic asthma," Allergy, 46:547-553, 1991.
Fanta et al., "Glucocorticoids in Acute Asthma," American Journal of Medicine, 74:845-851, 1983.
Hett et al., "Large-Scale Synthesis of Enantic—and Diasteromerically Pure (R,R)-Formoterol," *Org. Process Res. Dev.*, 2:96-99, 1998.
Li, "Key Points of the new asthma guidelines," The Journal of Respiratory Diseases, 18:823-838, 1997.
Maesen et al., "Bronchodilator effect of inhaled formoterol vs salbutamol over 12 hours," Chest, 97:590-594, 1990.
Maesen et al., "Formoterol in the treatment of Nocturnal Asthma," Chest, 98:866-870, 1990.
Marsac et al., "Inhaled beta adrenergic agonists and inhaled steroids in the treatment of asthma" Annals of Allergy, 63:220-224, 1989.
Nana et al., "High-Dose Inhaled Budesonide May Substitute for Oral Therapy After an Acute Asthma Attack," Journal of Asthma, 35:647-655, 1998.
National Asthma Education and Prevention Program, "Guidelines for the Diagnosis and Management of Asthma," Expert Panel Report Jul. 2, 1997 No. 97/4051.
The Patents Act 1953 Statutory Declaration of Charles Richard William Beasley, (1998).
The Patents Act 1953 Exhibit "CRWB1." (1998).
The Patents Act 1953 Exhibit "CRWB3." (1998).
The Patents Act 1953 Exhibit "CRWB4." (1998).
The Patents Act 1953 Exhibit "CRWB5." (1998).
The Patents Act 1953 Exhibit "CRWB6." (1998).
Pauwels et al., "Effect of Inhaled Formoterol and Budesonide on Exacerbations of Asthma," The New England J. of Medicine, 337:1405-1411, 1997.
Poitiek et al., "Comparison of formoterol, saslbutamol and salmeterol in methacholine-induced severe bronchoconstriction" $B_2$-Agonists in Methacholine-Induced Bronchoconstriction Eur Respir J., 13:988-992, 1999.
Resenborg et al., "Relative systemic dose potency and tolerability of inhaled formoterol and salbutamol in healthy subjects and asthmatics," Eur J. Clin Pharmacol., 56:363-370, 2000.
Ryrfeldt et al., "Pulmonary disposition of the potent glucocorticoid budesonide evaluated in an isolated rat lung model," Biochem Pharmacol., 38:17-22, 1989.
Schuh et al., "A Comparison of Inhaled Fluticasone and Oral Prednisone for Children with Severe Acute Asthma," New England Journal of Medicine, 343:689-694, 2000.
Sue et al., "A Comparison of Intravenous Hydrocortisone, Methylprednisolone, and Dexamethasone in Acute Bronchial Asthma," Annals of Allergy, 56:406-409, 1986.
Sykes et al., "A study of the duration of the bronchodilator effect of 12 ug and 24 ug of inhaled formoterol and 200 ug inhaled salbutamol in asthma," Respir. Med., 84:135-138, 1990.
Tattersfield et al. on behalf of the Facet International Study Group, "Exacerbations of Asthma," Am J Respir Crit Care Med, 160:594-599, 1999.
U.S. Department of Health and Human services, "Practical Guide for the Diagnosis and Management of Asthma," Oct. 1997 NIH Publication No. 97-4053.
Vanieleghem et al., "A comparison of budesonide and beclomethasone dipropionate nasal aerosols in ragweed-induced rhinitis'," J. Allergy Clin. Immunology, 79:887-892, 1987.
Submission dated Sep. 29, 2011 filed in the European Patent Office by opponent Norton Healthcare Ltd. in an opposition proceeding against European Patent No. 1 085 877 (14 pages).
The 1993 British Thoracic Society Guidelines for the Management of Asthma, as published in Thorax, vol. 48, supplement S1-S24 (1993).
G. Schultz-Werninghaus, "Long-term treatment with inhaled formoterol over one year", 8th Congress of the European Society of Pneumology, Sep. 1989, pp. 46-50, published 1990.
B. Lundback et al., "Twelve month comparison of salmeterol and salbutamol as dry powder formulations in asthmatic patients", Thorax, vol. 48, pp. 148-153 (1993).
P.J. Barnes et al., Ed., Asthma, Lippincott-Raven, USA, Chapter 126, vol. 2, pp. 1854-1857 (1997).
Statement of Professor Neil Christopher Barnes dated Jul. 26, 2011, filed in the European Patent Office opposition proceeding against European Patent No. 1 085 877, 5 pages.
Second Statement of Professor Neil Christopher Barnes dated Sep. 8, 2011, filed in the European Patent Office opposition proceeding against European Patent No. 1 085 877, 4 pages.
S. Kesten et al., "Sustained improvement in asthma with long-term use of formoterol fumarate," Annals of Allergy, vol. 69, pp. 415-420 (1992).
Greening et al. "Added salmeterol versus higher-dose corticosteroid in asthma patients with symptoms on existing inhaled corticosteroid," The Lancet, 344(8917): 219-224 (1994).
Midgren et al., "Formoterol, a new long-acting beta 2 agonist, inhaled twice daily, in stable asthmatic subjects," Chest, 101(4): 1019-1022 (1992).
Sears et al., "Regular inhaled beta-agonist treatment in bronchial asthma," The Lancet, 336(8728): 1391-1396 (1990).
Wegener et al., "Rapid onset of action of inhaled formoterol in asthmatic patients," Chest, 102(2): 535-538 (1992).
Falck et al., "Formoterol Turbuhaler 72 and 120 µg (delivered doses 54 and 90 µg, respectively) daily during three days was safe in patients with asthma," Eur Respir J., 10 Suppl 25:103s (1997).
Greening et al., "Added salmeterol versus higher-dose corticosteroid in asthma patients with symptoms on existing inhaled corticosteroid," The Lancet, 344(8917):219-224 (1994).
Wegener et al., "Rapid onset of action of inhaled Formoterol in asthmatic patients," Chest, 102(2):535-538 (1992).
Mikhail et al., "Is twice daily prophylaxis with salbutamol and beclomethasone dipropionate effective in the management of asthma?," Pharmatherapeutica, 4(10):648-654 (1986).
Selroos, "The pharmacologic and clinical properties of Oxis® (formoterol) Turbuhaler®," Allergy, 53:14-19 (1998).
Kraft and Martin, "Nocturnal Asthma," Chapter 135, Asthma, edited by P.J. Barnes, M.M. Grunstein, A.R. Leff and A.J. Woolcock, Lippincott-Raven Publishers, Philadelphia (1997).
Holgate (Ed.), "Formoterol: Fast and long lasting bronchodilatation," International Congress and Symposium Series No. 194, Royal Society of Medicine Services (1992).

\* cited by examiner

METHODS AND COMPOSITIONS FOR TREATING ASTHMA

This application is a continuation of application Ser. No. 09/367,950, filed Aug. 18, 1999 now abandoned, which is the National Stage of International Application No. PCT/SE99/01031, filed Jun. 10, 1999, which claims priority from Swedish Application No. 9802073-8, filed Jun. 11, 1998.

FIELD OF THE INVENTION

The present invention relates to use of a composition for symptomatic relief, when needed, comprising, in admixture
(a) a first active ingredient which is formoterol, a pharmaceutically acceptable salt or solvate thereof or a solvate of such a salt; and
(b) a second active ingredient which is budesonide;
for the manufacture of a medicament for use in the prevention or treatment of an acute condition of asthma and/or intermittent asthma and/or episodes in chronic asthma. The invention further relates to a method for prevention or treatment of an acute condition of asthma and/or intermittent asthma and/or episodes in chronic asthma by administering, by inhalation, a composition comprising the first and second active ingredients as defined previously.

BACKGROUND OF THE INVENTION

Despite recent advances in the awareness of asthma and the introduction of powerful and effective anti-asthma drugs, asthma remains a poorly understood and frequently poorly treated disease. There have been recent advances in the treatment of the disease which result from the recognition that asthma is a chronic inflammatory disease. Therapy is now aimed at both controlling the symptoms and reducing the inflammation. The symptoms may be controlled by $\beta_2$-adrenoceptor agonists such as terbutaline, salbutamol, formoterol and salmeterol. Prophylactic therapy is typically provided by steroids such as beclomethasone dipropionate, fluticasone propionate, mometasone furoate and budesonide.

In spite of modern maintenance treatment too many asthmatic patients are undertreated for a number of reasons with a negative impact on their quality of life. Too complicated therapy with different medications and devices may lead to misunderstanding and communication problems between patient and doctor. Poor compliance is a common phenomenon. Improved patient education may partly counteract this, but does not completely solve the problem. A new and more simple approach to asthma treatment could thus be of tremendous help for many patients suffering from respiratory disease, particularly asthma. The combination of budesonide and formoterol in the same device as suggested in PCT applications WO 93/11773 and WO 98/15280 (both to Astra AB of Sweden) offers a favorable pathway to improve today's asthma management with an excellent safety profile. However, although having an adequate regular, e.g. bid, treatment with such a combination, many patients will now and then run into acute situations with a higher frequency and severity of exacerbations, when additional medication is needed. Such an additional medication is often a $\beta_2$-adrenoceptor agonist with fast onset, normally terbutaline or salbutamol. A second medicament is thus needed, and this can negatively affect the overall compliance of the patient. There is thus need for a neat way of handling maintenance treatment together with the treatment of acute situations which.

SUMMARY OF THE INVENTION

It is an object of the present invention to provide use of a suitable composition for the manufacture of a medicament for the treatment of acute episodes of asthma as a complement to maintenance treatment.

More specifically, according to the invention there is provided use of a composition for symptomatic relief when needed comprising, in admixture
(a) a first active ingredient which is formoterol, a pharmaceutically acceptable salt or solvate thereof or a solvate of such a salt; and
(b) a second active ingredient which is budesonide;
for the manufacture of a medicament for use in the prevention or treatment of an acute condition of asthma and/or intermittent asthma and/or episodes in chronic asthma.

Use of the present composition, when needed, relates to use of said composition during one or more of the following conditions:
i) an acute condition of asthma, i.e. acute asthma attacks,
ii) intermittent asthma and/or
iii) short periods (episodes) of acute attacks of bronchospasms in chronic asthma.

Acute asthma attacks may occur on an irregular basis when exposed to an agent e.g. during the pollen season, a virus infection, cold air, perfumes or any other agent(s) triggering an asthma attack in the patient.

It lies within the scope of the present invention, to use the compositions comprising active compounds (a) and (b) for treating acute conditions of asthma, intermittent asthma and episodes in chronic asthma, in addition to treating chronic asthma on a regular basis, with the same active compounds (a) and (b) or one or more different active compounds, preferably selected from short-acting $\beta$-agonists, long-acting $\beta$-agonists and glucocorticosteroids.

We contemplate preventive use when the patient expects to encounter asthma inducing conditions e.g. intends to take exercise or go into smoky conditions.

According to a further aspect of the invention a method of prevention or treatment of an acute condition of asthma and/or intermittent asthma and/or episodes in chronic asthma, when needed, which comprises administering, by inhalation, to a patient an effective amount of a composition comprising, in admixture:
(a) a first active ingredient which is formoterol, a pharmaceutically acceptable salt or solvate thereof or a solvate of such a salt; and
(b) a second active ingredient which is budesonide.

According to the present invention it has surprisingly been found that the medicament can be administered when needed to a patient with an acute attack of asthma.

The recommended dose regimen described in the prior art as disclosed above is twice a day. This dose recommendation was a result of a concern not to have too high an administration of the active compounds. However, in the present invention it has been found that it is possible for the patient to administer this mixture as often as needed.

The combination of formoterol and budesonide can be used as a rescue medication. Worsening of symptoms can be counteracted by incremental use of the combination for symptom relief, e.g. during exacerbations with the additional steroid component coming in as early as possible to suppress the enhanced airway inflammation. The long duration of formoterol will reduce the risk of too frequent dosing. When taking the combination budesonide/formoterol when needed the severity of exacerbations can be reduced. The as needed use (Pro Re Nata, PRN) will also minimize the difficulty of predicting which patients will be controlled on a low dose of inhaled steroid rather than increasing the is steroid dose before adding a long-acting $\beta_2$-agonist. Under-treatment with inhaled glucocorticosteroids following a too low maintenance dose will be more or less "self-corrected" by the rescue usage according to the present invention. The PRN use of the combination will always give some beneficial anti-inflammatory effects even if it is used by the patient only for rescue purposes. A treatment for patients suffering from respiratory disease, particularly asthma (including allergic conditions, e.g. episodic or intermittent asthma), will therefore be to use the combination formoterol/budesonide for maintenance therapy as well as on an as needed basis (for rescue purposes), e.g. for prevention of exercise and/or allergen induced asthma.

DETAILED DESCRIPTION OF THE INVENTION

Formoterol is a compound which can exist in several stereochemical forms. The present invention includes the individual stereoisomers as well as mixtures thereof. It is intended that the present invention includes geometrical isomers, rotational isomers, racemates, diastereomers and enantiomers, in particular the R,R enantiomer of formoterol.

Suitable physiologically salts of formoterol include acid addition salts derived from inorganic and organic acids such as the hydrochloride, hydrobromide, sulfate, phosphate, maleate, fumarate, tartrate, citrate, benzoate, 4-methoxybenzoate, 2- or 4-hydroxybenzoate, 4-chlorobenzoate, p-toluenesulphonate, methanesulphonate, ascorbate, salicylate, acetate, succinate, lactate, glutarate, gluconate, tricarballylate, hydroxy-naphthalene-carboxylate or oleate. Formoterol is preferably used in the form of its fumarate salt and as a dihydrate of this salt.

The present invention also encompasses compositions comprising the 22R epimer of budesonide as the second active ingredient.

A suitable unit dose of formoterol (as fumarate dihydrate) is in the range of from 1 µg to 48 µg, preferably from 2 µg to 24 µg, and more preferably between 3 µg and 12 µg. The daily dose of formoterol (as fumarate dihydrate), including maintenance therapy, should be in the range of from 1 µg to 100 µg, preferably from 2 µg to 60 µg, and more preferably from 3 µg to of 48 µg.

A suitable unit dose of budesonide is in the range of from 20 µg to 1600 µg, suitably from 30 µg to 800 µg, preferably from 50 µg to 400 µg, and more preferably between 100 µg and 200 µg. The daily dose of budesonide, including maintenance therapy, should be in the range of 20 µg to 4800 µg, preferably from 30 µg to 3200 µg, and more preferably from 40 µg to 1600 µg. The particular dose regimen will depend on the patient (age, sex, weight etc.) and the severity of the disease (mild, moderate, severe asthma etc.).

The molar ratio of the first active ingredient (as formoterol) to the second active ingredient of the invention, suitably lies in the range of from 1:1 to 1:100, preferably from 1:1 to 1:70, and more preferably from 1:1 to 1:50.

Preferably the mixture comprises one or more pharmaceutically acceptable additives, diluents or carriers, more preferably in an amount of from 50 µg to 4000 µg in each dose, most preferably in an amount of from 100 µg to 2000 µg and most preferably from 100 µg to 1000 µG. Examples of suitable additives, diluents or carriers include lactose, dextran, mannitol or glucose. Preferably lactose is used, and more preferably as the monohydrate.

One or more of the ingredients of the mixture may be in the form of dry powder, more preferably a small particle dry powder, most preferably an agglomerated small particle dry powder. Alternatively one or more of the active ingredients (a) or (b) are in the form of an ordered mixture with diluent, additive or carrier. The ingredients used in the invention can be obtained in these preferred forms using methods known to those skilled in the art. The particle size of the active ingredients is preferably less than 10 µm.

Administration may be by inhalation orally or intranasally. The ingredients of the system are preferably adapted to be administered from a dry powder inhaler, a pressurized metered dose inhaler, or a nebulizer.

When the ingredients of the system are adapted to be administered from a pressurized inhaler, they are preferably in a small particle form. They are dissolved, or, preferably, suspended in a liquid propellant mixture. The propellants which can be used include chlorofluorocarbons, hydrocarbons or hydrofluorocarbons. Especially preferred, propellants are P134a (tetrafluoroethane), P152a (difluoroethane) and P227 (heptafluropropane) each of which may be used alone or in combination. They are optionally used in combination with one or more other propellants and/or one or more surfactants and/or one or more other excipients, for example ethanol, a lubricant, an antioxidant and/or a stabilizing agent.

When the ingredients of the system of the invention are adapted to be administered via a nebulizer they may be in the form of a nebulized aqueous suspension or solution, with or without suitable pH or tonicity adjustment, either as a unit dose or multidose formulation.

EXAMPLES

The ingredients can be formulated as illustrated by the following examples which are not intended to limit the scope of the invention.

In the examples micronization is carried out in a conventional manner such that the particle size range for each component is suitable for administration by inhalation. Turbuhaler® is a trademark of Astra AB.

Example 1

4.5 Parts by weight of formoterol fumarate dihydrate were mixed with 915 parts by weight of lactose monohydrate. The blend was micronized using a high pressure air jet mill and then conditioned using the process of EP-A-717 616. 80 Parts by weight of micronized budesonide were added to the conditioned product by mixing and homogenizing with a low pressure jet mill. The mixture was then spheronized using the process of EP-A-721 331 and filled into the storage compartment of Turbuhaler.®

Example 2

9 Parts by weight of formoterol fumarate dihydrate were mixed with 831 parts by weight of lactose monohydrate. The blend was micronized using a high pressure air jet mill and then conditioned using the process of EP-A-717 616. 160 Parts by weight of micronized budesonide were added to the conditioned product by mixing and homogenizing with a low pressure jet mill. The mixture was then spheronized using the process of EP-A-721 331 and filled into the storage compartment of Turbuhaler.®

Example 3

6 Parts by weight of formoterol fumarate dihydrate were mixed with 894 parts by weight of lactose monohydrate. The blend was micronized using a high pressure air jet mill and then conditioned using the process of EP-A-717 616. 100 Parts by weight of micronized budesonide were added to the conditioned product by mixing and homogenizing with a low pressure jet mill. The mixture was then spheronized using the process of EP-A-721 331 and filled into the storage compartment of Turbuhaler.®

Example 4

12 Parts by weight of formoterol fumarate dihydrate were mixed with 788 parts by weight of lactose monohydrate. The blend was micronized using a high pressure air jet mill and then conditioned using the process of EP-A-717 616. 200 Parts by weight of micronized budesonide were added to the conditioned product by mixing and homogenizing with a low pressure jet mill. The mixture was then spheronized using the process of EP-A-721 331 and filled into the storage compartment of Turbuhaler.®

Example 5

A patient on maintenance treatment with the fixed combination formoterol fumarate dihydrate/budesonide in a dose of 4.5/80 μg or 4.5/160 μg bid additionally uses the same combination either for rescue purposes once or twice daily to treat sporadic breakthrough symptoms, or as needed to treat exacerbations during one or two weeks, with a maximum daily dose of 36/640 μg (8 puffs of 4.5/80 μg) and 36/1280 μg (8 puffs of 4.5/160 μg), respectively.

Example 6

A patient with intermittent asthma uses the fixed combination formoterol fumarate dihydrate/budesonide as sole medication to be taken as needed until the asthma resolves. The highest recommended daily dose will be either 36/640 μg (8 puffs of 4.5/80 μg) or 36/1280 μg (8 puffs of 4.5/160 μg) for a period not exceeding 8-120 weeks. If symptoms still persist after that period of time—regular maintenance therapy should be considered.

The invention claimed is:

1. A method of treating asthma in a patient, the method comprising administering an effective amount of a composition comprising, in admixture:
   (a) a first active ingredient that is formoterol, a pharmaceutically acceptable salt or solvate thereof or a solvate of such a salt; and
   (b) a second active ingredient that is budesonide;
   characterized in that the patient is administered (i) a maintenance dose of the composition twice per day, on a regular basis, and (ii) one or more additional doses on an irregular basis, wherein the one or more additional doses are administered as-needed, as determined by the patient.

2. The method according to claim 1, wherein the molar ratio of (a) to (b) calculated as formoterol to budesonide is from 1:1 to 1:100.

3. The method according to claim 1, wherein the first active ingredient is formoterol fumarate dihydrate.

4. The method according to claim 1, wherein the first active ingredient is the R,R enantiomer of formoterol or a pharmaceutically acceptable salt or solvate of said enantiomer or a solvate of such a salt.

5. The method according to claim 3, wherein the composition is in the form of unit doses, each of which delivers 1 μg to 48 μg of the first active ingredient, calculated as formoterol fumarate dihydrate.

6. The method according to claim 3, wherein the patient is administered an amount per day of the composition, including for maintenance therapy, that contains a total of 1 μg to 100 μg of the first active ingredient, calculated as formoterol fumarate dihydrate.

7. The method according to claim 1, wherein the second active ingredient is the 22R epimer of budesonide.

8. The method according to claim 1, wherein the composition is in the form of unit doses, each of which delivers 20 μg to 1600 μg of budesonide to the patient.

9. The method according to claim 1, wherein the patient is administered an amount per day of the composition, including for maintenance therapy, that contains a total of 20 μg to 4800 μg of budesonide.

10. The method according to claim 1, wherein the particle size of the active ingredients (a) and (b) is less than 10 μm.

11. The method according to claim 1, wherein the composition additionally comprises one or more pharmaceutically acceptable additives, diluents or carriers.

12. The method according to claim 1, wherein the composition additionally comprises lactose monohydrate.

13. The method according to claim 2, wherein the molar ratio of (a) to (b) calculated as formoterol to budesonide is from 1:1 to 1:70.

14. The method according to claim 5, wherein the composition is in the form of unit doses, each of which delivers 3 μg to 12 μg of the first active ingredient to the patient, calculated as formoterol fumarate dihydrate.

15. The method according to claim 6, wherein the patient is administered an amount per day of the composition, including maintenance therapy, that contains a total of 2 μg to 60 μg of the first active ingredient, calculated as formoterol fumarate dihydrate.

16. The method according to claim 8, wherein the composition is in the form of unit doses, each of which delivers 50 μg to 400 μg of budesonide to the patient.

17. The method according to claim 9, wherein the patient is administered an amount per day of the composition, including maintenance therapy, that contains a total of 30 μg to 3200 μg of budesonide.

18. A method of treating asthma in a patient, the method comprising
   administering an effective amount of a composition comprising, in admixture:
   (a) a first active ingredient that is formoterol, a pharmaceutically acceptable salt or solvate thereof or a solvate of such a salt; and
   (b) a second active ingredient that is budesonide;
   characterized in that the patient is administered (i) a maintenance dose of the composition twice per day on a regular basis, and (ii) one or more additional doses on an irregular basis, wherein the one or more additional doses are administered when the patient expects to encounter an asthma inducing condition.

19. The method of claim 18 wherein the asthma inducing condition is selected from the group consisting of exercise, exposure to cold air, exposure to pollen, exposure to perfume, and exposure to a smoky environment.

20. A method of treating asthma in a patient, the method comprising
   administering an effective amount of a composition comprising, in admixture:
   (a) a first active ingredient that is formoterol, a pharmaceutically acceptable salt or solvate thereof or a solvate of such a salt; and
   (b) a second active ingredient that is budesonide;

characterized in that the patient is administered (i) a maintenance dose of the composition twice per day on a regular basis, and (ii) one or more additional doses, wherein the one or more additional doses are administered when the patient experiences an acute asthma attack.

21. The method of claim 1, wherein the first and second active ingredients are both in dry powder form.

22. The method of claim 1, wherein the composition is administered from a pressurized metered dose inhaler.

23. The method of claim 22, wherein the first and second active ingredients are suspended in a liquid propellant.

24. The method of claim 23, wherein the liquid propellant is one or more of tetrafluoroethane, difluoroethane, and heptafluoropropane.

25. The method of claim 23, wherein the liquid propellant is heptafluoropropane.

26. The method of claim 1, wherein the composition is administered by the patient.

27. A method of treating asthma in a patient, the method comprising administering an effective amount of a composition comprising, in admixture:
 (a) a first active ingredient that is formoterol, a pharmaceutically acceptable salt or solvate thereof or a solvate of such a salt; and
 (b) a second active ingredient that is budesonide;
 characterized in that the patient is administered (i) a maintenance dose of the composition twice per day on a regular basis, and (ii) one or more additional doses on an irregular basis, wherein the one or more additional doses are administered when needed for symptom relief.

28. A method of treating asthma in a patient, the method comprising administering an effective amount of a composition comprising, in admixture:
 (a) a first active ingredient that is formoterol, a pharmaceutically acceptable salt or solvate thereof or a solvate of such a salt; and
 (b) a second active ingredient that is budesonide;
 characterized in that the patient is administered (i) a maintenance dose of the composition on a regular basis as determined by the patient's physician, and (ii) one or more additional doses on an irregular basis, wherein the one or more additional doses are administered when the patient determines the additional dose or doses are needed for symptom relief or when the patient expects to encounter an asthma inducing condition.

29. The method of claim 18, wherein the first active ingredient is formoterol fumarate dihydrate.

30. The method of claim 20, wherein the first active ingredient is formoterol fumarate dihydrate.

31. The method of claim 27, wherein the first active ingredient is formoterol fumarate dihydrate.

32. The method of claim 28, wherein the first active ingredient is formoterol fumarate dihydrate.

33. The method of claim 1, wherein the composition is inhaled by the patient from an inhaler, and each puff from the inhaler delivers 4.5 µg formoterol fumarate dihydrate and 80 µg budesonide to the patient.

34. The method of claim 1, wherein the composition is inhaled by the patient from an inhaler, and each puff from the inhaler delivers 4.5 µg formoterol fumarate dihydrate and 160 µg budesonide to the patient.

35. The method of claim 18, wherein the composition is inhaled by the patient from an inhaler, and each puff from the inhaler delivers 4.5 µg formoterol fumarate dihydrate and 80 µg budesonide to the patient.

36. The method of claim 18, wherein the composition is inhaled by the patient from an inhaler, and each puff from the inhaler delivers 4.5 µg formoterol fumarate dihydrate and 160 µg budesonide to the patient.

37. The method of claim 20, wherein the composition is inhaled by the patient from an inhaler, and each puff from the inhaler delivers 4.5 µg formoterol fumarate dihydrate and 80 µg budesonide to the patient.

38. The method of claim 20, wherein the composition is inhaled by the patient from an inhaler, and each puff from the inhaler delivers 4.5 µg formoterol fumarate dihydrate and 160 µg budesonide to the patient.

39. The method of claim 27, wherein the composition is inhaled by the patient from an inhaler, and each puff from the inhaler delivers 4.5 µg formoterol fumarate dihydrate and 80 µg budesonide to the patient.

40. The method of claim 27, wherein the composition is inhaled by the patient from an inhaler, and each puff from the inhaler delivers 4.5 µg formoterol fumarate dihydrate and 160 µg budesonide to the patient.

41. The method of claim 28, wherein the composition is inhaled by the patient from an inhaler, and each puff from the inhaler delivers 4.5 µg formoterol fumarate dihydrate and 80 µg budesonide to the patient.

42. The method of claim 28, wherein the composition is inhaled by the patient from an inhaler, and each puff from the inhaler delivers 4.5 µg formoterol fumarate dihydrate and 160 µg budesonide to the patient.

* * * * *